(12) United States Patent
Nishimi et al.

(10) Patent No.: US 8,580,571 B2
(45) Date of Patent: Nov. 12, 2013

(54) METHOD FOR PRODUCING A BIOSENSOR

(75) Inventors: Taisei Nishimi, Kanagawa (JP); Koichi Kawamura, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 262 days.

(21) Appl. No.: 11/710,433

(22) Filed: Feb. 26, 2007

(65) Prior Publication Data

US 2007/0266775 A1 Nov. 22, 2007

(30) Foreign Application Priority Data

Feb. 27, 2006 (JP) ................................ 2006-049761

(51) Int. Cl.
*G01N 33/487* (2006.01)
*B05D 5/00* (2006.01)

(52) U.S. Cl.
USPC ........ 436/164; 73/53.01; 427/58; 204/403.01

(58) Field of Classification Search
USPC ........ 436/164; 73/53.01; 427/58; 204/403.01
See application file for complete search history.

(56) References Cited

FOREIGN PATENT DOCUMENTS

| JP | 2002-513153 A | 5/2002 |
| JP | 2005-277225 A | 10/2005 |
| JP | 2005 283142 A | 10/2005 |
| JP | 2005 283143 A | 10/2005 |
| WO | 03/046144 A2 | 6/2003 |
| WO | WO 03/046144 * | 6/2003 |
| WO | 2005/052580 A1 | 6/2005 |
| WO | 2005/095507 A1 | 10/2005 |

OTHER PUBLICATIONS

Muller, H.C., Nanstructuring of alkanethiols with ultrsharp field emitters(1995). Journal of Vacuum Science Technology B. 13:6. 2846-2849.*
Oswald Prucker, et al., "Photochemical Attachment of Polymer Films to Solid Surfaces via Monolayers of Benzophenone Derivatives". J. Am. Chem. Chem. Soc. 1999, vol. 121, No. 38, pp. 8766-8770, XP-002307406.
Extended European Search Report dated Jun. 13, 2007.
Office Action dated Mar. 1, 2011 on Japanese Application No. 2007-041607.
Lofas and Johnsson, "A Novel Hydrogel Matrix on Gold Surfaces in Surface Plasmon Resonance Sensors for Fast and Efficient Covalent Immobilization of Ligands". J. Chem. Soc., Chem. Commun., 21 (1990), pp. 1526-1528.
Office Action dated Aug. 2, 2011 on Japanese Application No. JP 2007-041607.
Applied Polymer Science, vol. 97, No. 1, pp. 158-164 (2005).

* cited by examiner

*Primary Examiner* — Krishnan S Menon
*Assistant Examiner* — Rebecca M Fritchman
(74) *Attorney, Agent, or Firm* — Sughrue Mion, PLLC

(57) ABSTRACT

Thus, the present invention provides a method for producing a biosensor comprising a substrate coated with a hydrophilic polymer, which comprises allowing a compound generating a reactive group as a result of external stimulus to bind to the surface of a substrate, and then giving external stimulus in a state where a hydrophilic polymer capable of forming a covalent bond with said reactive group is allowed to come into contact with the substrate, so that said hydrophilic polymer is allowed to bind to the substrate surface via a covalent bond with said reactive group.

20 Claims, 1 Drawing Sheet

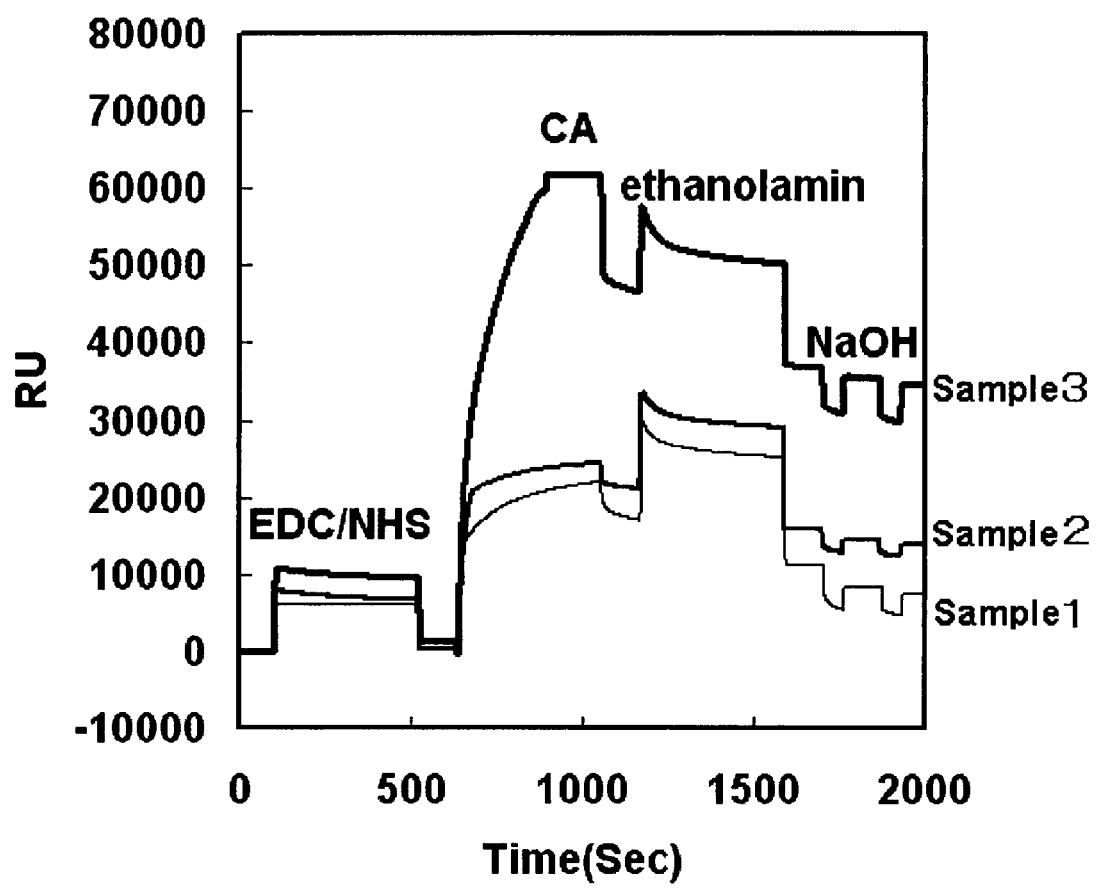

METHOD FOR PRODUCING A BIOSENSOR

TECHNICAL FIELD

The present invention relates to a method for producing a biosensor, and a method for analyzing an interaction between biomolecules using the above biosensor. In particular, the present invention relates to a method for producing a biosensor that is used as a surface plasmon resonance biosensor, and a method for analyzing an interaction between biomolecules using the above biosensor.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The QCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

Japanese Patent No. 2815120 discloses in detail a method for producing hydrogel, which is used as a detection surface having a functional group capable of immobilizing a physiologically active substance, for example. Specifically, a 16-mercaptohexadecanol layer binds to a gold film, so as to form a barrier layer. On the gold film, a hydroxyl group of the barrier layer is treated with epichlorohydrin so as to be epoxy-activated. In the subsequent step, dextran is allowed to bind to the barrier layer via an ether bond. Then, bromoacetic acid is allowed to react with a dextran matrix, resulting in introduction of a carboxymethyl group.

As a method for immobilizing a physiologically active substance having an amino group (e.g. a protein or amino acid) on the carboxymethyl degeneration dextran surface, which is produced by the above method, the following method has been disclosed. That is to say, a portion of carboxyl groups in carboxymethyl degeneration dextran are treated with an aqueous solution that contains N-hydroxysuccinimide (NHS) and N-(3-dimethylaminopropyl)-N'-ethyl-carbodiimide (EDC) hydrochloride, for example, so that such groups are degenerated so as to achieve a reactive ester function. Residual charge, that is, unreacted carboxyl groups would contribute to concentration of a physiologically active substance onto a detection surface. An aqueous solution of a physiologically active substance containing an amino group (a protein or amino acid) is allowed to come into contact with such a detection surface, so as to allow the physiologically active substance containing an amino group to bind to a dextran matrix via a covalent bond.

Since such hydrogel produced by the aforementioned method is able to immobilize a physiologically active substance containing an amino group in a three-dimensional manner, it has outstanding performance as a detection surface of biosensors. However, the aforementioned production method of hydrogel is complicated, and it requires a long production time. Further, since the above production method requires the use of compounds such as epichlorohydrin or bromoacetic acid, it has been problematic in terms of safety.

On the other hand, with regard to immobilization of a substance utilizing a photoreactive group, introduction of a photoreactive group (an azidophenyl group, etc.) into a polymer, so as to allow the polymer together with a protein to bind to a substrate (JP Patent Publication (Kokai) No. 2004-125781A), introduction of a photoreactive group (benzophenone) into a substrate, so as to allow a hydrophobic polymer (polystyrene, polyethyloxazolidine) to bind to the substrate (J. Am. Chem. Soc., 121, 8766 (1999)), immobilization of a DNA fragment on a solid surface via a graft polymer, so as to produce a DNA chip (JP Patent Publication (Kokai) No. 2003-130878A), and the like, have been reported.

DISCLOSURE OF THE INVENTION

It is an object of the present invention to solve the aforementioned problems of the prior art techniques. In other words, it is an object of the present invention to provide a method for easily immobilizing on the surface of a biosensor, hydrogel capable of immobilizing a physiologically active substance, using a safe raw material; and a biosensor produced by the aforementioned method.

As a result of concentrated studies directed towards achieving the aforementioned object, the present inventors have found that a compound that generates a reactive group as a result of external stimulus is allowed to bind to the surface of a sensor substrate, and such external stimulus is then given to the substrate in a state where a hydrophilic polymer capable of forming a covalent bond with the above described reactive group has been allowed to come into contact with the above described substrate, so as to easily produce a biosensor surface to which a hydrophilic polymer has bound, thereby completing the present invention.

Thus, the present invention provides a method for producing a biosensor comprising a substrate coated with a hydrophilic polymer, which comprises allowing a compound generating a reactive group as a result of external stimulus to bind to the surface of a substrate, and then giving external stimulus in a state where a hydrophilic polymer capable of forming a covalent bond with said reactive group is allowed to come into contact with the substrate, so that said hydrophilic polymer is allowed to bind to the substrate surface via a covalent bond with said reactive group.

Preferably, the compound generating a reactive group as a result of external stimulus is a photo radical generator.

Preferably, the hydrophilic polymer has a double bond.

Preferably, the hydrophilic polymer has a carboxyl group.

Preferably, the polymer containing a carboxyl group is a polysaccharide.

Preferably, the polymer containing a carboxyl group has a mean molecular weight between 1,000 and 5,000,000.

Preferably, the hydrophilic polymer is allowed to bind to a reactive group generated as a result of external stimulus in a state where a thin film of said polymer is formed on the substrate.

Preferably, the thin film is formed on the substrate by a spin coating method or a spray coating method.

Preferably, the substrate is a metal surface or a metal film.

Preferably, the metal is gold, silver, copper, platinum, or aluminum.

Another aspect of the present invention provides a biosensor produced by the aforementioned method of the present invention.

Preferably, the biosensor of the present invention is used in non-electrochemical detection, and more preferably is used in surface plasmon resonance analysis.

Another aspect of the present invention provides a method for immobilizing a physiologically active substance on a biosensor, which comprises a step of allowing the aforementioned biosensor of the present invention to come into contact with a physiologically active substance, so as to allow said physiologically active substance to bind to said biosensor.

Another aspect of the present invention provides a method for detecting or measuring a substance interacting with a physiologically active substance, which comprises a step of allowing the biosensor of the present invention, to the surface of which said physiologically active substance is bound via a covalent bond, to come into contact with a test substance.

Preferably, a substance interacting with the physiologically active substance is detected or measured by a non-electrochemical method, and is more preferably detected or measured by surface plasmon resonance analysis.

BRIEF DESCRIPTION OF THE DRAWING

FIG. 1 shows a sensorgram obtained by setting samples 1 to 3 produced in Example 3 in a surface plasmon resonance device, supplying each of an EDC/NHS solution, a CA solution, and an ethanolamine solution thereto for 5 minutes, and then supplying NaOH thereto.

BEST MODE FOR CARRYING OUT THE INVENTION

The embodiment of the present invention is described in detail below.

The biosensor of the present invention has as broad a meaning as possible, and the term biosensor is used herein to mean a sensor, which converts an interaction ein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/ coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

In the biosensor of the present invention, a metal surface or metal film can be used as a substrate. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

In the present invention, onto a biosensor surface, that is, onto a metal film, a compound generating a reactive group as a result of external stimulus is bound. Such a compound generating a reactive group as a result of external stimulus may be either a compound generating a radical by heat (a heat radical generator), or a compound generating a radical by light (a photo radical generator). Moreover, such a compound may also be a compound that is known as a photoaffinity labeling reagent.

As a heat radical generator, a known polymerization initiator, a compound having a bond whose bond dissociation energy is small, and the like, can be used. Examples of such a heat radical generator may include an organic halogenated compound, a carbonyl compound, an organic peroxide, an azo polymerization initiator, an azide compound, a metallocene compound, a hexaaryl biimidazole compound, an organic boric acid compound, a disulfonic acid compound, an oxime ester compound, and an onium salt compound. These heat radical generators may be used either singly or in combination of two or more types. Specific compound skeletons of such a heat radical generator are disclosed in chemical formulas 4 to 14 of JP Patent Publication (Kokai) No. 2005-335366A.

A photo radical generator has a single bond that is cleaved by light. Examples of such a single bond that is cleaved by light may include single bonds that are capable of being cleaved by utilizing carbonyl α and β cleavage reactions, a photo-Fries rearrangement reaction, a phenacyl ester cleavage reaction, a sulfonimide cleavage reaction, a sulfonyl ester cleavage reaction, an N-hydroxysulfonyl ester cleavage reaction, a benzylimide cleavage reaction, an active halogenated compound cleavage reaction, or the like. A single bond, which can be cleaved by light, is cut off by these reactions. Examples of such a single bond, which can be cleaved, may include a C—C bond, a C—N bond, a C—O bond, a C—Cl bond, an N—O bond, and an S—N bond. Examples of a group having a single bond that is cleaved by light may include an aromatic ketone group, a phenacyl ester group, a sulfonimide group, a sulfonyl ester group, an N-hydroxysulfonyl ester group, a benzylimide group, a trichloromethyl group, and a benzyl chloride group.

In addition, a photo radical generator preferably has a reactive group (a substrate-binding group), which reacts with a functional group existing on the surface of a substrate and is able to bind thereto. A specific example of such a reactive group is the following group:

Q: substrate-binding group —SiO(OMe)₃—SiCl₃—NCO—CH₂Cl

A group having a single bond that is cleaved by light may directly bind to a substrate-binding group, or may bind thereto via a linking group. Examples of the linking group may include linking groups containing an atom selected from the group consisting of a carbon atom, a nitrogen atom, an oxygen atom, and a sulfur atom. Specific examples of the linking group may include a saturated carbon group, an aromatic group, an ester group, an amide group, a ureido group, an ether group, an amino group, and a sulfonamide group. Moreover, the linking group may also have a substituent. Examples of the introducible substituent may include an alkyl group, an alkoxy group, and a halogen atom.

These photo radical generators may be used either singly or in combination of two or more types. Specific compound skeletons of the photo radical generator are disclosed in chemical formulas 2 to 4 of JP Patent Publication (Kokai) No. 2005-277225A, but examples are not limited thereto.

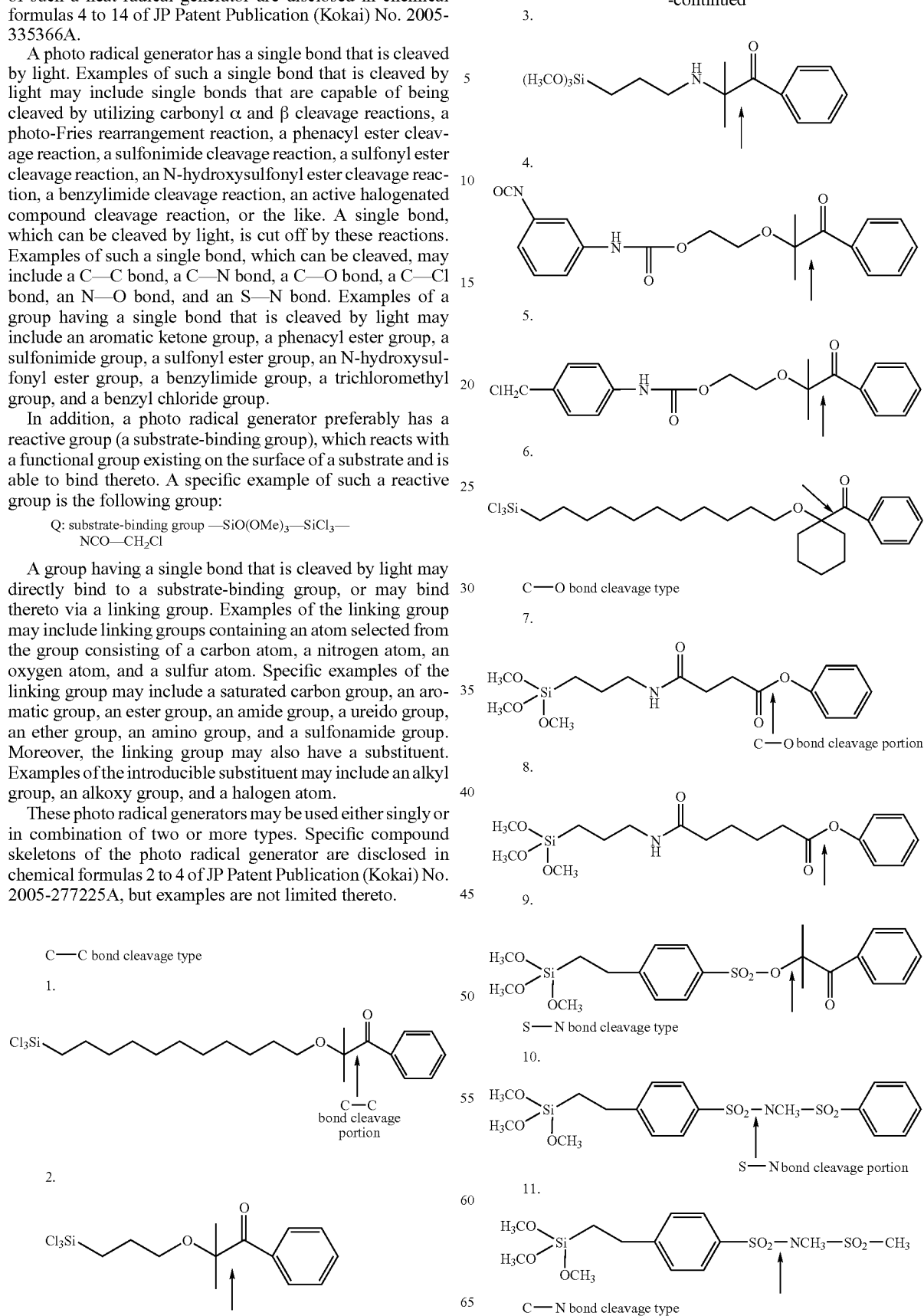

12.

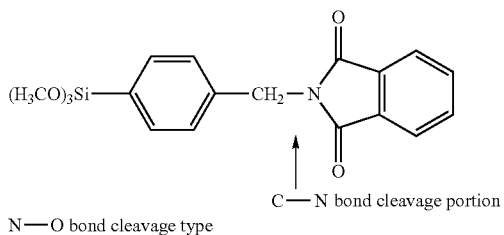

N—O bond cleavage type

13.

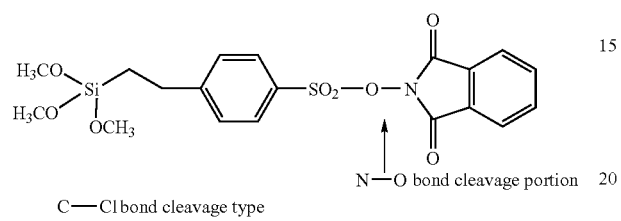

C—Cl bond cleavage type

14.

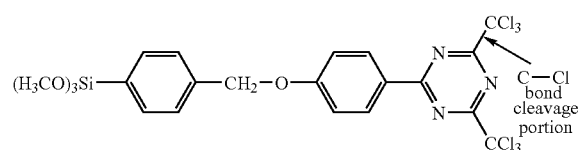

15.

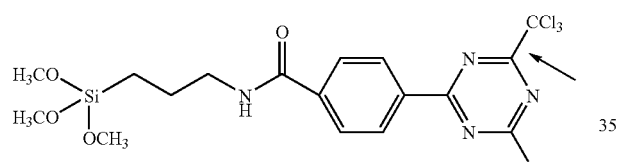

16.

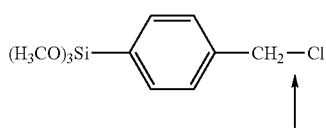

As a compound generating a reactive group as a result of light irradiation, a compound used in photoaffinity labeling can also preferably be used. Examples of active species generated from a photoaffinity labeling compound as a result of light irradiation may include nitrene, carbene, radical, ion radical, diradical, excited triplet, and a carbon electrophilic reagent such as carbocation. Examples of a photoaffinity labeling compound that generates such active species as a result of light irradiation are described in Summary of S. A. Flemig, Tetrahedron, Vol. 51, pp. 12479-12520, 1995, and Summary of Yasumaru Hatanaka, Journal of Synthetic Organic Chemistry, Japan, Vol. 56, pp. 581-590, 1998, for example. That is to say, examples of a compound generating nitrene may include compounds having an azide group, such as aromatic azide, alkyl azide, or heterocyclic azide. Examples of a compound generating carbene may include compounds having a diazo group or a diazirine ring. Examples of a compound generating a radical may include conjugated ketones such as benzophenones or enones, aromatic halides, and olefins. Examples of a compound generating a carbon nucleophilic reagent may include an aromatic diazonium salt, nitrobenzenes, a sulfonium salt, a phosphonium salt, and an ammonium salt. Since these photoreactive compounds have their own characteristics, they may be selected and used depending on use conditions. From the viewpoint of relatively high safety, a compound having a diazirine ring is preferable. From the viewpoint of safety and the ease of synthesis, conjugated ketones, aromatic halides, olefins, and the like are preferable. These photoaffinity labeling compounds may be used singly or in combination of two or more types. Specific compound skeletons of such photoaffinity labeling compounds include the following skeletons described in chemical formula 3 of JP Patent Publication (Kokai) No. 2004-301681A, but examples are not limited thereto.

A-1

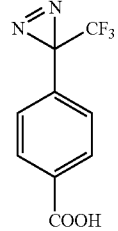

A-2

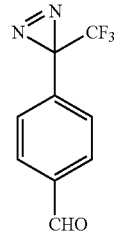

A-3

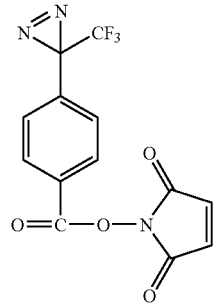

A-4

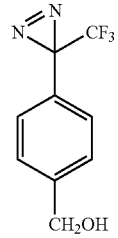

A-5

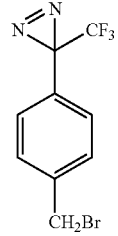

-continued

A-6 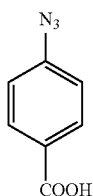

A-7 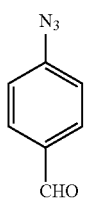

A-8 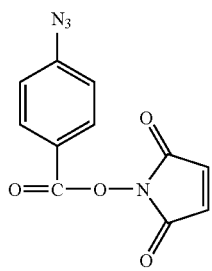

A-9 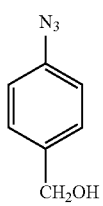

A-10 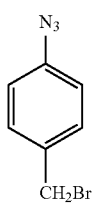

A-11 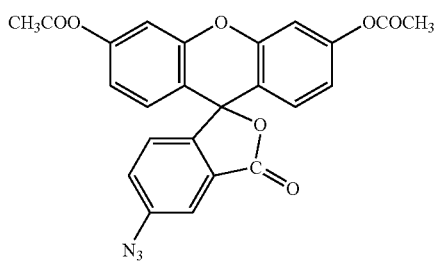

A-12 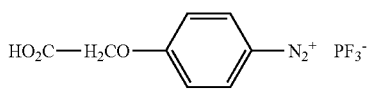

A-13 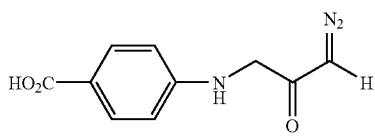

-continued

A-14 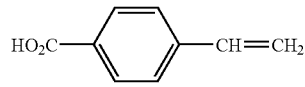

A-15 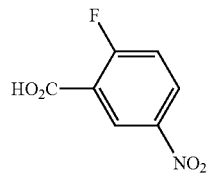

A-16 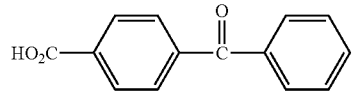

In terms of easy patterning on the surface of a substrate, a compound generating a reactive group as a result of external stimulus is preferably a photo radical generator or a photoaffinity labeling compound.

In the present invention, a compound generating a reactive group as a result of external stimulus preferably binds to a metal film coated with a self-assembled monolayer. A method of coating metal films with self-assembled monolayers (SAMs) has been intensively studied by Professor Whitesides at Harvard University, and the details thereof are described in Chemical Review, 105, 1103-1169 (2005), for example. When gold is used as metal, an alkanethiol derivative represented by formula 1 (wherein n represents an integer between 3 and 20, and X represents a functional group) is used as an organic layer-forming compound, so that a monomolecular film having orientation can be formed in a self-assemble manner, based on an Au—S bond and the van der Waals force between alkyl chains. A self-assembled monolayer is produced by an extremely easy method, which comprises immersion of a gold substrate in a solution of an alkanethiol derivative. From the viewpoint of easy bindability of a reactive group due to external stimulus, it is preferable to use a self-assembled monolayer having an amino group in the present invention. By forming a self-assembled monolayer using a compound wherein $X=NH_2$ in formula 1, it becomes possible to coat a gold surface with an organic layer having an amino group.

1

Alkanethiol having an amino group at the terminus thereof may be either a compound wherein a thiol group is connected with an amino group via an alkyl chain (formula 2) (in formula 2, n represents an integer between 3 and 20), or a compound obtained by allowing alkanethiol having a carboxyl group at the terminus thereof (formulas 3 and 4) (in formula 3, n represents an integer between 3 and 20, and in formula 4, n independently represents an integer between 1 and 20) to react with an excessive amount of hydrazide or polyamine. Such a reaction between alkanethiol having a carboxyl group at the terminus thereof and an excessive amount of hydrazide or polyamine may be carried out in a solution state. Otherwise, after alkanethiol having a carboxyl group at the terminus thereof has been allowed to bind to the surface of a substrate, an excessive amount of hydrazide or polyamine may be allowed to react therewith.

$$HS(CH_2)_nNH_2 \quad (2)$$

$$HS(CH_2)_nCOOH \quad (3)$$

$$HS(CH_2)_n(OCH_2CH_2)_nOCH_2COOH \quad (4)$$

Specific examples of polyamine that can be preferably used in the present invention may include: aliphatic diamines such as ethylenediamine, tetraethylenediamine, octamethylenediamine, decamethylenediamine, piperazine, triethylenediamine, diethylenetriamine, triethylenetetramine, dihexamethylenetriamine, or 1,4-diaminocyclohexane; aromatic diamines such as paraphenylene diamine, metaphenylenediamine, paraxylylenediamine, metaxylylenediamine, 4,4'-diaminobiphenyl, 4,4'-diaminodiphenylmethane, 4,4'-diaminodiphenylketone, or 4,4'-diaminodiphenylsulfonic acid; and polyamines such as diethylenetriamine, triethylenetetramine, tetraethylenepentamine, pentaethylenehexamine, spermidine, spermine, or polyethyleneimine. From the viewpoint of the improvement of hydrophilicity on the biosensor surface, a compound wherein two amino groups are connected with each other via an ethylene glycol unit (formula 5) may also be used.

$$H_2N(CH_2)_n(OCH_2CH_2)_mO(CH_2)_nNH_2 \quad (5)$$

Alkanethiol having an amino group can also form a self-assembled monolayer by itself. Otherwise, such alkanethiol can be mixed with another alkanethiol, so as to form a self-assembled monolayer. When such an alkanethiol is used as a biosensor surface, a compound capable of suppressing non-specific adsorption of a physiologically active substance is preferably used as another alkanethiol. Such a self-assembled monolayer capable of suppressing non-specific adsorption of a physiologically active substance has been studied in detail by the aforementioned Professor Whitesides et al. Professor Whitesides et al. have reported that a self-assembled monolayer formed from alkanethiol having a hydrophilic group is effective for suppression of non-specific adsorption (Langmuir, 17, 2841-2850, 5605-5620, 6336-6343 (2001)). In the present invention, as alkanethiol forming a mixed monomolecular film together with alkanethiol having an amino group, a compound described in the aforementioned article can be preferably used. In terms of excellent ability to suppress non-specific adsorption and availability, examples of such alkanethiol forming a mixed monomolecular film together with alkanethiol having an amino group that is preferably used may include alkanethiol having a hydroxyl group (formula 6) and alkanethiol having an ethylene glycol unit (formula 7) (in formula 6, n represents an integer between 3 and 20, and in formula 7, n and m independently represent an integer between 1 and 20).

$$HS(CH_2)_nOH \quad (6)$$

$$HS(CH_2)_n(OCH_2CH_2)_mOH \quad (7)$$

In the present invention, it is possible to mix alkanethiol having an amino group with alkanethiol having a hydrophilic group at any given ratio. When the ratio of alkanethiol having an amino group is small, the binding amount of a polymer that contains an active esterified carboxyl group is decreased. When the ratio of alkanethiol having a hydrophilic group is small, ability to suppress non-specific adsorption is reduced. Accordingly, the mixing ratio between alkanethiol having an amino group and alkanethiol having a hydrophilic group is preferably between 1/1 and 1/1,000,000, more preferably between 1/4 and 1/10,000, and further more preferably between 1/10 and 1/1,000. From the viewpoint of a reduction in steric hindrance occurring during a reaction with a polymer containing an active esterified carboxyl group, the molecular length of alkanethiol having an amino group is preferably longer than that of alkanethiol having a hydrophilic group.

As alkanethiol used in the present invention, a compound synthesized based on the summary of Professor Grzybowski at Northwestern University (Curr. Org. Chem., 8, 1763-1797 (2004)) and the cited documents thereof may be used, or a commercially available compound may also be used. Such compounds are available from Dojindo Laboratories, Aldrich, SensoPath Technologies, Frontier Scientific Inc., etc. A disulfide compound that is the oxidation product of alkanethiol can be used as with alkanethiol in the present invention.

As a hydrophilic polymer that can be used in the present invention, a known compound can be used. When the use as a sensor surface is considered, such a hydrophilic polymer is preferably a polymer containing a carboxyl group, which is able to form a covalent bond together with the amino group of a physiologically active substance. Such a hydrophilic polymer should covalently bind to a reactive group generated as a result of external stimulus. Accordingly, such a hydrophilic polymer preferably has a C—H bond that enables hydrogen abstraction, an unsaturated double bond, or a functional group such as an epoxy group or an oxetane group. From the viewpoint of synthesis, a hydrophilic polymer, into which a double bond has been introduced, is preferable. Utilizing a reaction with functional groups such as a carboxyl group, an amino group or a salt thereof, a hydroxyl group, or an ethoxy group, which exist in a hydrophilic polymer, it becomes possible to introduce a double bond into a hydrophilic polymer. Examples of a compound used to introduce a double bond in this reaction may include (meth)acrylic acid, glycidyl (meth)acrylate, allyl glycidyl ether, 2-isocyanatoethyl (meth)acrylate, and 2-aminoethyl (meth)acrylate. Other than these compounds, there is also a method of introducing a functional group such as 2-methyl-2-bromopropionic acid and then introducing a double bond by treating with a base.

As a polymer containing a carboxyl group used in the present invention, a carboxyl group-containing synthetic polymer and a carboxyl group-containing polysaccharide can be used. Examples of such a carboxyl group-containing synthetic polymer may include polyacrylic acid, polymethacrylic acid, and their copolymers such as a methacrylic acid copolymer, an acrylic acid polymer, an itaconic acid copolymer, a crotonic acid copolymer, a maleic acid copolymer, a partially esterified maleic acid copolymer, and a polymer having a hydroxyl group to which an acid anhydride is added, which are described in JP Patent Publication (Kokai) No. 59-44615A (1984), JP Patent Publication (Kokoku) Nos. 54-34327B (1979), 58-12577B (1983) and 54-25957B (1979), and JP Patent Publication (Kokai) Nos. 59-53836A (1984) and 59-71048A (1984). Such a carboxyl group-containing polysaccharide may be any one selected from an extract from natural plants, a product obtained by fermentation by microorganisms, a synthetic product obtained by enzymes, and a chemically synthetic product. Specific examples of such a carboxyl group-containing polysaccharide may include hyaluronic acid, chondroitin sulfuric acid, heparin, dermatan sulfate, carboxymethyl cellulose, carboxyethyl cellulose, cellouronic acid, carboxymethyl chitin, carboxymethyl dextran, and carboxymethyl starch. As a carboxyl group-containing polysaccharide, a commercially available product can be used. Specific examples of such a carboxyl group-containing polysaccharide may include CMD, CMD-L and CMD-D40 (manufactured by Meito Sangyo Co., Ltd.), which are carboxymethyl dextrans, carboxymethylcellulose sodium (manufactured by Wako Pure Chemical Industries, Ltd.), and sodium alginate (manufactured by Wako Pure Chemical Industries, Ltd.).

A polymer containing a carboxyl group is preferably a polysaccharide containing a carboxyl group, and more preferably carboxymethyl dextran.

The molecular weight of the polymer containing a carboxyl group used in the present invention is not particularly limited. The mean molecular weight is preferably between 1,000 and 5,000,000, more preferably between 10,000 and 2,000,000, and further more preferably between 100,000 and 1,000,000. When the mean molecular weight is smaller than the above described range, the amount of a physiologically active substance immobilized becomes small. When the mean molecular weight is larger than the above described range, it causes a high solution viscosity, and it thereby becomes hard to deal with it.

In the present invention, a hydrophilic polymer, which is in the form of a solution, may be allowed to react with a substrate. Otherwise, it may also be allowed to react therewith in a state where a thin film has been formed on a substrate by methods such as spin coating. The reaction is preferably carried out in a state where a thin film has been formed is preferable.

As stated above, the hydrophilic polymer of the present invention may be preferably allowed to react with a substrate in the state of a thin film. As a method for forming a thin film on a substrate, known methods can be used. Specific examples of such methods that can be used include an extrusion coating method, a curtain coating method, a casting method, a screen printing method, a spin coating method, a spray coating method, a slide bead coating method, a slit and spin method, a slit coating method, a dye coating method, a dip coating method, a knife coating method, a blade coating method, a flow coating method, a roll coating method, a wire-bar coating method, and a transfer printing method. These methods for forming a thin film are described in "Progress in Coating Technology (*Coating Gijutsu no Shinpo*)" written by Yuji Harazaki, Sogo Gyutsu Center (1988); "Coating Technology (*Coating Gijutsu*)" Technical Information Institute Co., Ltd. (1999); "Aqueous Coating Technology (*Suisei Coating no Gijutsu*)" CMC (2001); "Evolving Organic Thin Film: Edition for Deposition (*Shinka-suru Organic Thin Film: Seimaku hen*)" Sumibe Techno Research Co., Ltd. (2004); "Polymer Surface Processing Technology (*Polymer Hyomen Kako Gaku*)" written by Akira Iwarnori, Gihodo Shuppan Co., Ltd. (2005); and the like. As the method for forming a thin film on a substrate of the present invention, a spray coating method or a spin coating method is preferable. Further, a spin coating method is more preferable. This is because it allows a coating film having a controlled film thickness to be readily produced.

The spray coating method is a method wherein a substrate is moved with an ultra-atomized polymer solution sprayed onto the substrate to thereby uniformly coat the polymer solution onto the substrate. When the trigger of a spray gun is pulled, an air valve and a needle valve are simultaneously opened. The polymer solution is ejected in the form of a fine mist from a nozzle, and this polymer solution in the form of a fine mist is further ultra-atomized by air ejected from an air cap located at the end of the nozzle. A thickness-controlled polymer film is easily produced by forming the coating film of the ultra-atomized polymer solution on the substrate surface, followed by the evaporation of the solvent. The thickness of the polymer thin film can be controlled on the basis of the concentration of the polymer solution, the moving speed of the substrate, and so on.

The spin coating method is a method wherein a polymer solution is added dropwise onto a substrate placed horizontally, which is then spun at a high speed to thereby uniformly coat the polymer solution onto the whole surface of the substrate through a centrifugal force. A thickness-controlled polymer film is easily produced with the scattering of the polymer solution through a centrifugal force and the evaporation of the solvent. The thickness of the polymer thin film can be controlled on the basis of the revolution speed, the concentration of the polymer solution, the vapor pressure of the solvent, and so on. In the present invention, the revolution speed during spin coating is not particularly limited. If the revolution speed is too small, the solution remains on the substrate. If the revolution speed is too large, an available apparatus is restricted. Hence, in the present study, the revolution speed during spin coating is preferably 500 rpm to 10,000 rpm, more preferably 1,000 rpm to 7,000 rpm.

A polymer containing a carboxyl group is activated by a known method using water-soluble carbodiimide, 1-(3-dimethylaminopropyl)-3 ethylcarbodiimide (EDC), and N-hydroxysuccinimide (NHS), for example, so that it is able to immobilize a physiologically active substance having an amino group. As a method of activating carboxylic acid, the method described in Japanese Patent Application No. 2004-238396 (JP Patent Publication (Kokai) No. 2006-58071A) (that is, a method of activating a carboxyl group existing on the surface of a substrate using any compound selected from a uronium salt, a phosphonium salt, and a triazine derivative, which have a specific structure, so as to form a carboxylic amide group) and the method described in Japanese Patent Application No. 2004-275012 (JP Patent Publication (Kokai) No. 2006-90781A) (that is, a method, which comprises activating a carboxyl group existing on the surface of a substrate using a carbodiimide derivative or a salt thereof, converting the resultant to an ester using any compound selected from a nitrogen-containing hetero aromatic compound having a hydroxyl group, a phenol derivative having an electron attracting group, and an aromatic compound having a thiol group, and allowing the ester to react with amine, so as to form a carboxylic amide group) can preferably be used.

It is to be noted that the aforementioned uronium salt, phosphonium salt, and triazine derivative, which have a specific structure, described in Japanese Patent Application No. 2004-238396 (JP Patent Publication (Kokai) No. 2006-58071A), mean the uronium salt represented by the following formula 1, the phosphonium salt represented by the following formula 2, and the triazine derivative represented by the following formula 3, respectively.

formula 1

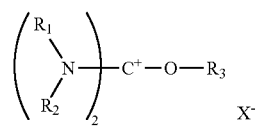

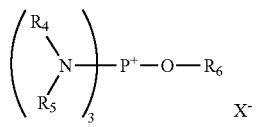

formula 2

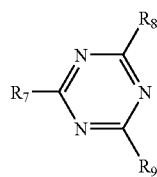

formula 3

(in formula 1, each of $R_1$ and $R_2$ independently represents an alkyl group containing 1 to 6 carbon atoms, or $R_1$ and $R_2$ together form an alkylene group containing 2 to 6 carbon atoms, which forms a ring together with an N atom, $R_3$ represents an aromatic ring group containing 6 to 20 carbon atoms, or a hetero ring group containing at least one heteroatom, and $X^-$ represents an anion; in formula 2, each of $R_4$ and $R_5$ independently represents an alkyl group containing 1 to 6 carbon atoms, or $R_4$ and $R_5$ together form an alkylene group containing 2 to 6 carbon atoms, which forms a ring together with an N atom, $R_6$ represents an aromatic ring group containing 6 to 20 carbon atoms, or a hetero ring group containing at least one heteroatom, and $X^-$ represents an anion; and in formula 3, $R_7$ represents an onium group, and each of $R_8$ and $R_9$ independently represents an electron donating group.)

A physiologically active substance immobilized on the surface for the biosensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

A biosensor to which a physiologically active substance is immobilized as described above can be used to detect and/or measure a substance which interacts with the physiologically active substance.

In the present invention, it is preferable to detect and/or measure an interaction between a physiologically active substance immobilized on the substrate for sensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta SP$), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta SP$) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta SP$) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle ($\theta SP$) is measured periodically when a certain period of time has elapsed.

If the test substance contained in the sample solution is bound to the sensing substance, the refractive index of the sensing substance is changed by this binding over time. Accordingly, the above attenuated total reflection angle ($\theta SP$) is measured periodically after the elapse of a certain time, and it is determined whether or not a change has occurred in the above attenuated total reflection angle ($\theta SP$), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle ($\theta$SP). For example, a sample solution may be added to a sensing substance, and the amount of an attenuated total reflection angle ($\theta$SP) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle ($\theta$SP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle ($\theta$SP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example 1

Synthesis of Photo Radical Generator (Compound A)

(1) Synthesis of Intermediate 1

29.33 g (0.150 mol) of 4-cyano-4'-hydroxybiphenyl and 75 ml of N,N-dimethylacetamide were placed in a 300-ml three-necked flask equipped with a cooling tube, and the mixture was then stirred, so as to prepare a homogeneous solution. Thereafter, 22.81 g (0.165 mol) of potassium carbonate was added to the above solution, and the mixture was then heated to 80° C. in an oil bath. Thereafter, 38.78 g (0.166 mol) of 11-bromo-1-undecene was gradually added dropwise to the above mixture. 1.5 hours later, the reaction solution was heated to 100° C., and the reaction was further continued for 1.5 hours. Disappearance of the raw material was confirmed by TLC. After completion of the reaction, 230 ml of water was added to the reaction solution, and the precipitated white solid was collected by filtration and was then washed with water. The obtained solid was recrystallized from acetonitrile, so as to obtain 43.11 g of intermediate 1. The yield was found to be 82.6%.

(2) Synthesis of Intermediate 2

20.00 g (57.56 mmol) of intermediate 1 was placed in a 300-ml three-necked flask equipped with a calcium chloride tube, and it was then dissolved in 150 g (1.0 mol) of trichloroacetonitrile under cooling on ice, so as to prepare a homogeneous solution. Thereafter, 1.54 g (5.76 mmol) of aluminum bromide was added to the above solution, and hydrochloric acid gas was then bubbled through the solution, while the solution was stirred. After the solution had been further stirred for 4 hours, it was left at rest overnight. The obtained product was extracted with ethyl acetate, and it was then subjected to column chromatography (hexane/ethyl acetate=3/1) to isolate intermediate 2. It was found that the recovered amount was 36.44 g, and that the yield was 99.5%.

(3) Synthesis of Compound A 2.01 g (3.159 mmol) of intermediate (B) was placed in a 50-ml three-necked flask equipped with a calcium chloride tube, and it was then dissolved in 3 ml of tetrahydrofuran. The obtained solution was cooled to 0° C. Thereafter, 6 ml of trichlorosilane was then added thereto, and the obtained mixture was then stirred. Thereafter, a Speir catalyst (platinic chloride hexahydrate/2-propanol, 0.1 M) was added thereto, and the obtained mixture was continuously stirred at room temperature. 5 hours later, unreacted trichlorosilane was distilled away under reduced pressure, so as to obtain compound A.

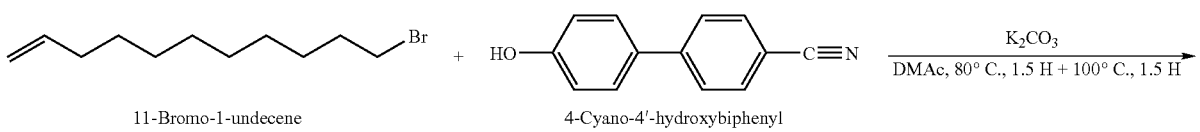

11-Bromo-1-undecene      4-Cyano-4'-hydroxybiphenyl

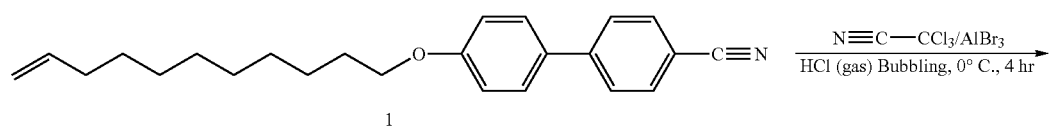

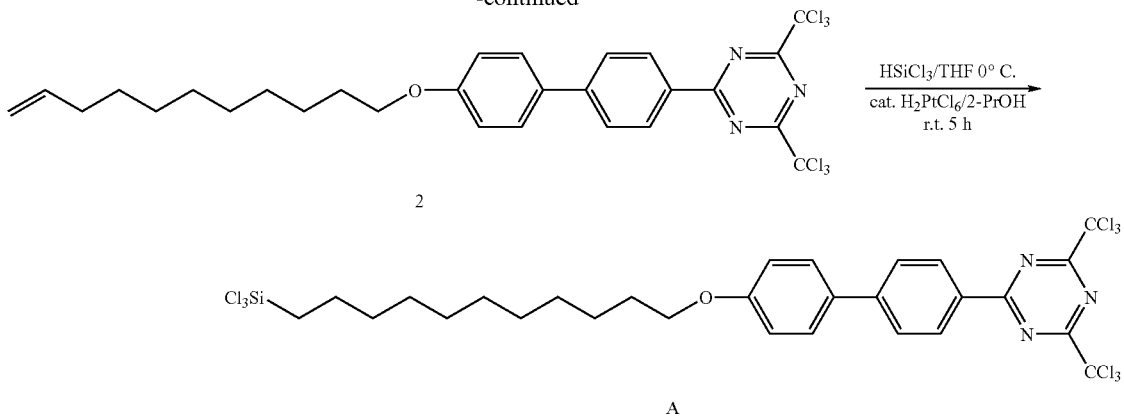

Example 2

Introduction of Double Bond into CMD

Compound 1

5.0 g of carboxymethyl dextran (abbreviated name: CMD-D40; manufactured by Meito Sangyo Co., Ltd.; molecular weight: 40,000) (0.02 mol/1 unit, 0.02 mol/sodium carboxylate) and 3.7 g (0.02 mol) of 2-aminoethyl methacrylate hydrochloride (90%) were dissolved in 40 g of distilled water. Thereafter, the obtained solution was cooled in an ice bath, and 4.2 g (0.022 mol) of 1-ethyl-3-(3-dimethylaminopropyl)-carbodiimide hydrochloride (abbreviated name: WSC; manufactured by Dojindo Laboratories) dissolved in 12 g of distilled water was then added thereto. The obtained mixture was stirred at room temperature overnight, and the reaction solution was then added to 500 ml of acetone. The precipitated solid was collected by filtration. The obtained solid was reslurried with methanol, and it was then dried, so as to obtain 4.1 g of light brown powders. The structure was confirmed by NMR. As a result, it was found that approximately 20 mol % of sodium carboxylate contained in CMD-D40 was reacted with 2-aminoethyl methacrylate, so that it was amidated.

Compound 2

5.0 g of carboxymethyl dextran (abbreviated name: CMD-D40; manufactured by Meito Sangyo Co., Ltd.; molecular weight: 40,000) (0.02 mol/1 unit, 0.02 mol/sodium carboxylate) and 1.8 g (0.01 mol) of 2-aminoethyl methacrylate hydrochloride (90%) were dissolved in 40 g of distilled water. Thereafter, the obtained solution was cooled in an ice bath, and 2.1 g (0.011 mol) of 1-ethyl-3-(3-dimethylaminopropyl)-carbodiimide hydrochloride (abbreviated name: WSC; manufactured by Dojindo Laboratories) dissolved in 12 g of distilled water was then added thereto. The obtained mixture was stirred at room temperature overnight, and the reaction solution was then added to 500 ml of acetone. The precipitated solid was collected by filtration. The obtained solid was reslurried with methanol, and it was then dried, so as to obtain light brown powders. The structure was confirmed by NMR. As a result, it was found that approximately 8 mol % of sodium carboxylate contained in CMD-D40 was reacted with 2-aminoethyl methacrylate, so that it was amidated.

Compound 3

5.0 g of carboxymethyl dextran (abbreviated name: CMD; manufactured by Meito Sangyo Co., Ltd.; molecular weight: 1,000,000) (0.02 mol/1 unit, 0.013 mol/sodium carboxylate) and 2.4 g (0.013 mol) of 2-aminoethyl methacrylate hydrochloride (90%) were dissolved in 320 g of distilled water. Thereafter, the obtained solution was cooled in an ice bath, and 2.7 g (0.0143 mol) of 1-ethyl-3-(3-dimethylaminopropyl)-carbodiimide hydrochloride (abbreviated name: WSC; manufactured by Dojindo Laboratories) dissolved in 12 g of distilled water was then added thereto. The obtained mixture was stirred at room temperature overnight, and the reaction solution was then added to 3,000 ml of acetone. The precipitated solid was collected by filtration. The obtained solid was reslurried with methanol, and it was then dried, so as to obtain 4.6 g of light brown powders. The structure was confirmed by NMR. As a result, it was found that 9.4 mol % of sodium carboxylate contained in CMD was reacted with 2-aminoethyl methacrylate, so that it was amidated.

Compound 4

1.0 g of carboxymethyl dextran (abbreviated name: CMD; manufactured by Meito Sangyo Co., Ltd.; molecular weight: 1,000,000) ($4 \times 10^{-3}$ mol/1 unit, $2.5 \times 10^{-3}$ mol/sodium carboxylate) and 0.92 g ($5.0 \times 10^{-3}$ mol) of 2-aminoethyl methacrylate hydrochloride (90%) were dissolved in 100 g of distilled water. Thereafter, the obtained solution was cooled in an ice bath, and 1.05 g ($5.5 \times 10^{-3}$ mol) of 1-ethyl-3-(3-dimethylaminopropyl)-carbodiimide hydrochloride (abbreviated name: WSC; manufactured by Dojindo Laboratories) dissolved in 5 g of distilled water was then added thereto. The obtained mixture was stirred at room temperature overnight, and the reaction solution was then added to 2,000 ml of acetonitrile. The precipitated solid was collected by decantation. The obtained solid was reslurried with methanol, and it was then dried, so as to obtain 0.94 g of light brown powders. The structure was confirmed by NMR. As a result, it was found that 13.7 mol % of sodium carboxylate contained in CMD was reacted with 2-aminoethyl methacrylate, so that it was amidated.

Compound 5

1.0 g of carboxymethyl dextran (abbreviated name: CMD; manufactured by Meito Sangyo Co., Ltd.; molecular weight: 1,000,000) ($4 \times 10^{-3}$ mol/1 unit, $2.5 \times 10^{-3}$ mol/sodium carboxylate) and 1.84 g ($10.0 \times 10^{-3}$ mol) of 2-aminoethyl methacrylate hydrochloride (90%) were dissolved in 100 g of distilled water. Thereafter, the obtained solution was cooled in an ice bath, and 2.11 g ($11.0 \times 10^{-3}$ mol) of 1-ethyl-3-(3-dimethylaminopropyl)-carbodiimide hydrochloride (abbreviated name: WSC; manufactured by Dojindo Laboratories) dissolved in 5 g of distilled water was then added thereto. The reaction solution was then added to 2,000 ml of acetonitrile. The precipitated solid was collected by decantation. The obtained solid was reslurried with methanol, and it was then dried, so as to obtain 0.89 g of light brown powders. The structure was confirmed by NMR. As a result, it was found that 18.2 mol % of sodium carboxylate contained in CMD was reacted with 2-aminoethyl methacrylate, so that it was amidated.

Example 3

The present example relates to production of a sensor chip for immobilizing a protein.
(1) Production of Sample 1 (Comparative Example)
The sensor chip CM-5 (research grade) of Biacore was directly used as sample 1 that was a surface to which carboxymethyl dextran bound.
(2) Production of Sample 2 (the Present Invention)
(2-1) Production of Substrate Having Amino Group
An experiment was carried out using the sensor chip Au of Biacore as a surface wherein only a gold film was formed on the sensor chip. The sensor chip Au was treated with UV ozone for 12 minutes. Thereafter, the resultant sensor chip was reacted at 40° C. for 1 hour in a solution prepared by dissolving 45 μmol of 11-hydroxy-1-undecanethiol (manufactured by Aldrich) and 4 μmol of 16-mercaptohexadecanoic acid (manufactured by Aldrich) in 8 ml of ethanol and 2 ml of extra pure water. Thereafter, the sensor chip was washed with ethanol once, and with extra pure water once. Subsequently, 100 μl of a mixed solution consisting of EDC (0.4 M)/NHS (0.1 M) was added dropwise onto the above substrate, and it was then reacted at room temperature for 15 minutes for activation. Thereafter, the substrate was washed with extra pure water once. Thereafter, 50 μl of 1,2-bis(aminoethoxy) ethane was added dropwise to the above substrate, and it was then reacted at room temperature for 1 hour, followed by washing with extra pure water once.
(2-2) Binding of Photo Radical Generator (Compound A)
Compound A was dissolved in anhydrous MEK, so as to prepare a 0.5 wt % solution. A gold chip produced in (2-1) was spin-coated with a photo initiator solution (1,000 rpm; 20 sec), and it was then dried (80° C.; 5 minutes). Thereafter, MEK was applied to the chip, so as to wash the surface thereof.
(2-3) Photoimmobilization of Compound 2 on Gold Substrate
0.4 g of compound 2 was dissolved in 1.0 g of acetonitrile and 2.0 g of water, so as to prepare a 12 wt % solution. The solution was filtrated with a syringe-type filter, so as to eliminate insoluble matters. A gold chip surface, on which a photo initiator had been immobilized, was spin-coated with the thus obtained solution (750 rpm; 20 sec), and it was then dried (80° C.; 2 minutes), so as to prepare a dry film. Using a UV exposure apparatus UVX-02516S1LP01 (high pressure mercury lamp; manufactured by USHIO), the film was exposed for 1 minute, and it was then immersed in water for 48 hours for development, so as to obtain sample 2.
(3) Production of Sample 3 (The Present Invention)
0.05 g of compound 3 was dissolved in 5.0 g of water, 1 droplet of a saturated saline solution, and 1.5 g of acetonitrile, so as to prepare a 0.76 wt % solution. The thus obtained solution was applied onto the surface of the gold chip produced in (3-2) using a bar #36, and it was then dried (80° C.; 2 minutes), so as to prepare a dry film. Using a UV exposure apparatus UVX-02516S1LP01 (high pressure mercury lamp; manufactured by USHIO), the film was exposed for 0.5 minutes and 1 minute, and it was then immersed in water for 12 hours for development. In addition, a polymer remaining on the surface was removed by washing with underwater ultrasound for 5 minutes.

Example 4

The present example relates to immobilization of a protein on the sensor chip obtained in Example 3. As a protein, CA (Carbonic Anhydrase; manufactured by SIGMA) was used. It was confirmed that the isoelectric point of the used CA was approximately 5.8 by comparing with the simultaneously measured marker (Broad pI Kit; pH 3.5-9.3; manufactured by Amersham Biosciences) in an electrophoresis experiment using AE-8150 of ATTO. 10 μl was weighed from a solution prepared by dissolving 1 mg of CA in 1 ml of an HBS-EP buffer (manufactured by Biacore; 0.01 M HEPES, pH 7.4, 0.15M NaCl, 0.005% Surfactant P20, 3 mM EDTA). Thereafter, 90 μl of an acetate buffer (manufactured by Biacore; pH 5.0) was added to the above solution, so as to prepare a 0.1 mg/ml CA solution (pH 5.0; 0.1 mg/ml).

Each of samples 1 to 3 produced in Example 3 was set in Biacore 3000, a surface plasmon resonance device manufactured by Biacore. Thereafter, each of an aqueous solution containing 0.4 M EDC and 0.1 M NHS, a CA solution (pH 5.0; 0.1 mg/ml), and an ethanolamine solution (Biacore) was supplied for 5 minutes, and 10 mM NaOH was then supplied for 1 minute×2 times. Immobilization was examined in this case. As a running buffer, an HBS-N buffer (manufactured by Biacore; 0.01 M HEPES, pH 7.4, 0.15 M NaCl) was used. The obtained sensorgram is shown in FIG. 1.

The amounts of CA immobilized were 7757 RU (sample 1: comparative example), 13983 RU (sample 2: the present invention), and 34807 RU (sample 3: the present invention). Thus, it was proved that a CMD-bound surface having a protein immobilized amount that is greater than that of a commercially available CMD-bound surface can be easily produced by the present invention.

INDUSTRIAL APPLICABILITY

According to the present invention, it has become possible to easily immobilize hydrogel capable of immobilizing a physiologically active substance on a biosensor surface, using a safe raw material.

The invention claimed is:
1. A method for producing a biosensor comprising a substrate to which a hydrophilic polymer is being bound, the method comprising the steps of:
    (a) forming a self-assembled monolayer on a substrate, wherein the self-assembled monolayer is formed by an alkanethiol;
    (b) coating a solution containing a photo radical generator onto the substrate obtained in step (a) to allow the photo radical generator to bind to the self-assembled monolayer on the substrate, and then drying said substrate,
    (c) then coating a solution containing a hydrophilic polymer onto the substrate obtained in step (b), and then drying said substrate, wherein the hydrophilic polymer is a polysaccharide having a carboxyl group and a double bond and
    (d) exposing the substrate obtained in step (c) to a light to generate a reactive group from the photo radical generator and to covalently bind the hydrophilic polymer to said reactive group via the double bond of the hydrophilic polymer, whereby the biosensor comprising a substrate to which a hydrophilic polymer is being bound is produced,
    wherein the carboxyl group contained in the hydrophilic polymer bound to the substrate in the biosensor is used for immobilizing a physiologically active substance of interest onto the biosensor.
2. The method according to claim 1, wherein the hydrophilic polymer containing a carboxyl group has a mean molecular weight between 1,000 and 5,000,000.

3. The method according to claim 1, wherein, in step (c), a thin film of the hydrophilic polymer is formed on the substrate, and, in step (d), the thin film of the hydrophilic polymer is exposed to the light.

4. The method according to claim 3, wherein the thin film is formed on the substrate by a spin coating method or a spray coating method.

5. The method according to claim 1, wherein the substrate is a metal surface or a metal film.

6. The method according to claim 5, wherein the metal is gold, silver, copper, platinum, or aluminum.

7. A biosensor produced by the method according to claim 1.

8. The biosensor according to claim 7, which detects or measures via non-electrochemical detection.

9. The biosensor according to claim 7, which detects or measures via surface plasmon resonance analysis.

10. A method for immobilizing a physiologically active substance on a biosensor, which comprises a step of allowing the biosensor of claim 7 to come into contact with a physiologically active substance, so as to allow said physiologically active substance to bind to said biosensor.

11. A method for detecting or measuring a substance interacting with a physiologically active substance, which comprises a step of allowing the biosensor of claim 7, to the surface of which said physiologically active substance is bound via a covalent bond, to come into contact with a test substance.

12. The method according to claim 11, wherein a substance interacting with the physiologically active substance is detected or measured by a non-electrochemical method.

13. The method according to claim 11, wherein a substance interacting with the physiologically active substance is detected or measured by surface plasmon resonance analysis.

14. The method according to claim 1, wherein the photo radical generator has a single bond that is cleaved by light.

15. The method according to claim 14, wherein the photo radical generator is any of a C—C bond cleavage type, a C—N bond cleavage type, a C—O bond cleavage type, a C—Cl bond cleavage type, an N—O bond cleavage type, and an S—N bond cleavage type.

16. The method according to claim 1, wherein the hydrophilic polymer is a carboxymethyl dextran having a double bond.

17. The method according to claim 1, wherein the photo radical generator is at least one selected from the group consisting of compounds represented by formulas (1) to (17):

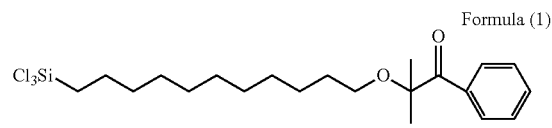
Formula (1)

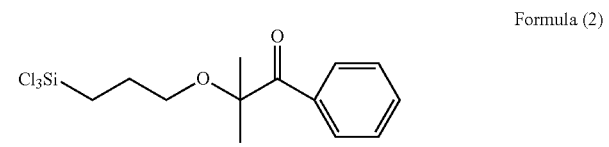
Formula (2)

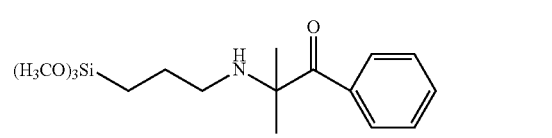
Formula (3)

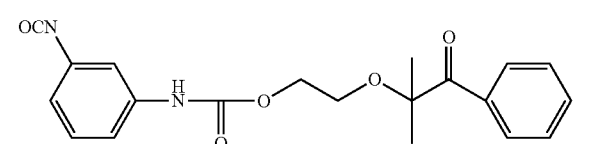
Formula (4)

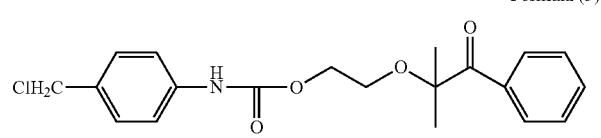
Formula (5)

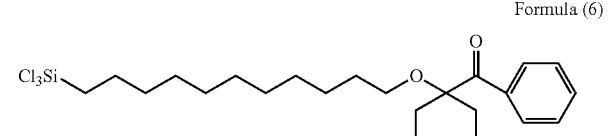
Formula (6)

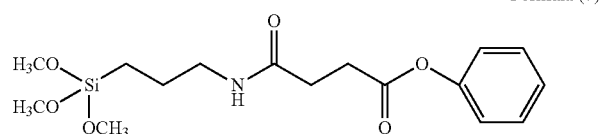
Formula (7)

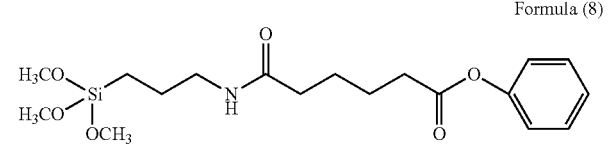
Formula (8)

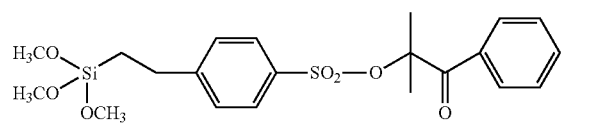
Formula (9)

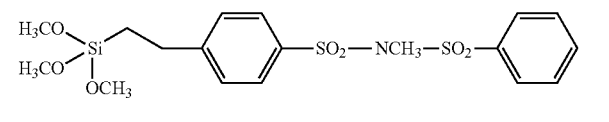
Formula (10)

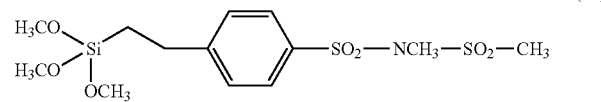
Formula (11)

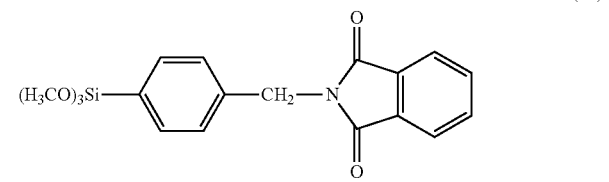
Formula (12)

-continued

Formula (13)
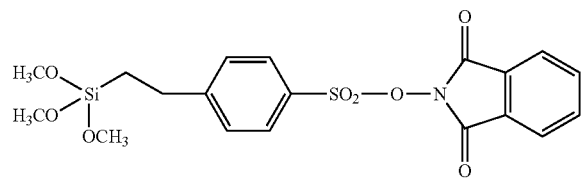

Formula (14)
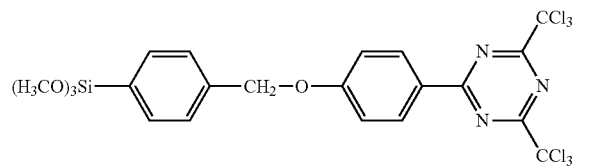

Formula (15)
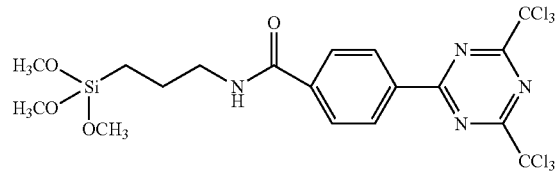

Formula (16)
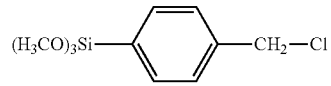

Formula (17)
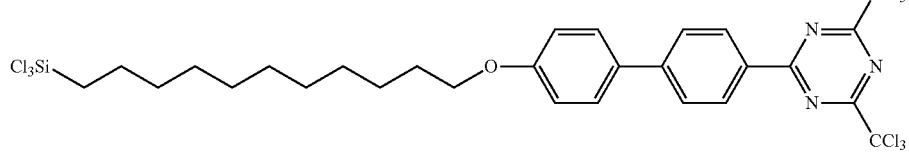

18. The method according to claim 1, wherein the hydrophilic polymer is at least one polysaccharide selected from the group consisting of hyaluronic acid, chondroitin sulfuric acid, heparin, dermatan sulfate, carboxymethyl cellulose, carboxyethyl cellulose, cellouronic acid, carboxymethyl chitin, carboxymethyl dextran, carboxymethyl starch, carboxymethylcellulose sodium, and sodium alginate.

19. The method according to claim 1, wherein the double bond contained in the hydrophilic polymer is a double bond that has been introduced into the hydrophilic polymer by reacting a carboxyl group, an amino group or a salt thereof, a hydroxyl group and/or an epoxy group present in the hydrophilic polymer with a compound selected from the group consisting of (meth)acrylic acid, glycidyl (meth)acrylate, allyl glycidyl ether, 2-isocyanaoethyl (meth)acrylate, and 2-aminoethyl (meth)acrylate.

20. The method according to claim 1, further comprising: reacting a carboxyl group, an amino group or a salt thereof, a hydroxyl group and/or an epoxy group present in the hydrophilic polymer with a compound selected from the group consisting of (meth)acrylic acid, glycidyl (meth)acrylate, allyl glycidyl ether, 2-isocyanatoethyl (meth)acrylate, and 2-aminoethyl (meth)acrylate to introduce the double bond into the hydrophilic polymer.

* * * * *